United States Patent
Hirao et al.

(10) Patent No.: US 7,109,372 B2
(45) Date of Patent: *Sep. 19, 2006

(54) METHOD FOR PRODUCTION OF ACRYLIC ACID

(75) Inventors: Harunori Hirao, Hyogo (JP); Yukihiro Matsumoto, Hyogo (JP); Kenji Sanada, Hyogo (JP); Takeshi Nishimura, Hyogo (JP)

(73) Assignee: Nippon Shokubai Co., LTD, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/633,170

(22) Filed: Aug. 1, 2003

(65) Prior Publication Data

US 2004/0063998 A1 Apr. 1, 2004

(30) Foreign Application Priority Data

Aug. 8, 2002 (JP) ............................ 2002-231448

(51) Int. Cl.
*C07C 51/16* (2006.01)
(52) U.S. Cl. ...................... 562/546; 562/600
(58) Field of Classification Search ............... 562/512, 562/598; 560/129
See application file for complete search history.

(56) References Cited

U.S. PATENT DOCUMENTS

| 4,203,906 A | 5/1980 | Takada et al. ........... 260/346.4 |
| 4,873,368 A * | 10/1989 | Kadowaki et al. .......... 562/532 |
| 6,384,274 B1 * | 5/2002 | Elder et al. ................. 562/532 |
| 2001/0021788 A1 | 9/2001 | Matsumoto et al. ........ 562/532 |

FOREIGN PATENT DOCUMENTS

| EP | 0 990 636 A1 | 4/2000 |
| EP | 1 116 709 A1 | 7/2001 |

* cited by examiner

*Primary Examiner*—Johann Richter
*Assistant Examiner*—Karl Puttlitz
(74) *Attorney, Agent, or Firm*—Mathews, Shepherd, McKay & Bruneau, P.A.

(57) ABSTRACT

A method is disclosed which produces acrylic acid in a high yield as maintaining the conditions for purifying acrylic acid in constant ranges and preventing the acrylic acid from polymerization. By using single a single reactor, propylene concentration adjusting in the range of 7–15 vol. % and water concentration adjusting in the range of 0–10 vol. % are introduced thereinto thereby obtaining an acrylic acid-containing gas. Then the gas is introduced to an acrylic acid absorption column to adjust water concentration in the range of 1–45 wt. %, thereby preventing from polymerization.

5 Claims, 1 Drawing Sheet

METHOD FOR PRODUCTION OF ACRYLIC ACID

BACKGROUND OF THE INVENTION

1. Field of the Invention

This invention relates to a method for producing acrylic acid comprising introducing propylene as a raw material in high concentration into a reactor which has a first reaction zone and a second reaction zone formed by dividing with at least one perforated tube plate, and improving water concentration in an acrylic acid-containing solution in an acrylic acid absorption column to a level in the range of 1–45 wt. %, thereby preventing the solution from polymerization at the subsequent steps in the process of the production.

2. Description of the Related Art

Acrylic acid is used in coating material, fiber processing, leather processing, and building material besides being used for acrylic fiber copolymer or as an emulsion for adhesive agents. The demand for this compound is now increasing. Thus, it is generally produced by the reaction of catalytic gas phase oxidation of propylene, for example, with a view to realizing the principle of mass production using an inexpensive raw material. The raw material gas is generally supplied at a concentration in the range of about 4–7 vol. % because the reaction of catalytic gas phase oxidation has the possibility of belonging to the range of explosion, depending on the proportion of molecular oxygen to be used in the reaction of oxidation. Since the raw material gas is preferred to be used at a high concentration for the purpose of improving the efficiency of production, various modifications have been proposed for the supply of the raw material gas at a high concentration.

The official gazette of JP-A-2000-103761, for example, discloses a method for producing acrylic acid from propylene by supplying a reaction composition comprising more than 7 vol. % of propylene, molecular oxygen, steam, and the balance of inert gas to a reactor furnished with two reaction zones packed with a catalyst and having a multiplicity of reaction tubes duly distributed therein. When the mixed product gas obtained by the reaction of catalytic gas phase oxidation is introduced into an absorber to obtain an aqueous acrylic acid solution, the exhaust gas of the absorber contains unreacted propylene, unreacted acrolein, and acrylic acid as residues. When this exhaust gas is put to cyclic use, the coefficient of absorption is depressed and the yield of acrylic acid is degraded because the volume of the inert gas flowing through the absorber is increased thereby being generated a load in the top of the absorber. Conversely, when the exhaust gas is not put to cyclic use, the water content in the gas flowing through the absorber is varied because the selectivity, the ratio of addition, and the catalytic activity in the reaction of oxidation are affected by the water content owing to the use of steam as a diluting gas. The method disclosed in the official gazette mentioned above contemplates reducing the load exerted on the absorber by using propylene of higher concentration than usual heretofore in the system of a single reactor and decreasing the exhaust gas of the absorber held as necessary for the sake of dilution.

Incidentally, after the absorption of the acrylic acid-containing gas, such purification steps as the dehydration of the acrylic acid-containing solution and the separation of low boiling substance and high boiling substance contained therein are carried out.

Acrylic acid, however, is an easily polymerizing compound. When the raw material gas of high concentration is used with a view to heightening the productivity of the method, this method is liable to generate an acrylic acid polymer at the step for absorbing acrylic acid and the subsequent step for purification of the absorbed acrylic acid. Since various columns for purificating continue production of acrylic acid while preventing occurrence of polymerization by adjusting such factors as the pressure of distillation, temperature, and amount of feed, the control of these factors is not easy because changes in these conditions affect other conditions. When the concentration of acrylic acid is depressed by a variation in the composition of the bottom liquid of an absorption column, for example, the maintenance of distillation conditions in a high acrylic acid concentration entails generation of an acrylic acid polymer in a distilling column. Though it is not to the extent of requiring forced suspension of the operation due to blockage, but possibly results in degrading the quality of acrylic acid produced due to the inclusion of the polymer and consequently depressing the yield of the product.

The purification step of acrylic acid is accomplished more often than not by adopting distilling columns called a dehydrating column, a light ends cut column, and a heavy ends cut column, concatenating the plurality of distilling columns endowed with different functions, and operating them jointly thereby performing a series of purification. Thus, the control of this purification step is rendered further difficult by the fact that a variation in the composition of the bottom liquid of any one of such distilling columns necessitates a due change in the purification conditions of the subsequent steps.

The solution, the exhaust gas, and the like which are discharged from the step for producing acrylic acid at times contain the raw material compound, the product, and other useful compounds. The cyclic use of such discharged substances in the process of production, therefore, can improve the yield of production. The composition of the exhaust gas, for example, is varied as with the distillation conditions and the generation of the polymer proceeds like a chain reaction. In the method for the production of acrylic acid particularly included a step for recycling the exhaust gas, therefore, it is extremely difficult to control the distillation conditions constant.

SUMMARY OF THE INVENTION

The present inventor has found that when in a process for the production of acrylic acid from propylene as a raw material the conditions in a reactor from the reaction of catalytic gas phase oxidation to the absorption of acrylic acid in an acrylic acid absorption column are restricted within specific ranges, the acrylic acid can be produced with high productivity from propylene of high concentration in the reactor and the operation of the process for purification can be simplified. This invention has been perfected on the basis of this knowledge.

Particularly by limiting the water content in the bottom liquid of the absorption column in the range of 1–45 wt. %, the occurrence of a polymer at the subsequent steps of the process can be effectively prevented. This control of the water content can be attained by adjusting the amount of an absorbent. By effecting this control in a more specific section of the range of 1–45 wt. %, it is made possible to narrow the width of control of the distillation conditions at the subsequent steps, restrain the fluctuations of loss of acrylic acid in the absorption column and a waste water generated from the process respectively to the minimum, and secure the stability of operation at the subsequent steps including the equipment for the treatment of the waste water.

It has been found that the adjustment of the concentration of absorption particularly by the variation of the amount of the absorbent in the absorption column results in enabling acrylic acid to be absorbed at a high concentration without changing the amount of the water discharged from the top of the absorption column and this adjustment, particularly when the exhaust gas of the absorption column is put to cyclic use, is at an advantage in stabilizing the conditions of production.

According to this invention, in the process for producing acrylic acid from propylene as the raw material having a step of the reaction of catalytic gas phase oxidation using a reactor having a first reaction zone and a second reaction zone thereof formed by dividing reaction tubes with at least one perforated tube plate and a step of the step for absorbing acrylic acid, by restricting in specific ranges the conditions in the operation of production, it is made possible to produce acrylic acid with high productivity from propylene gas of high concentration in the reactor and facilitate the operation in the process of purification as well.

Particularly the treatments at the subsequent steps can be rendered simple and easy by adjusting the water content of the bottom liquid of the absorption column in the range of 1–45 wt. %.

When the amount of the absorbent to be supplied in the absorption column is varied, the acrylic acid can be discharged at a high concentration without changing the amount of the water absorbed from the top of the absorption column. This variation brings an excellent effect of stabilizing the conditions of production particularly when the exhaust gas of the absorption column is put to cyclic use.

DESCRIPTION OF THE PREFERRED EMBODIMENTS

Figure 1:
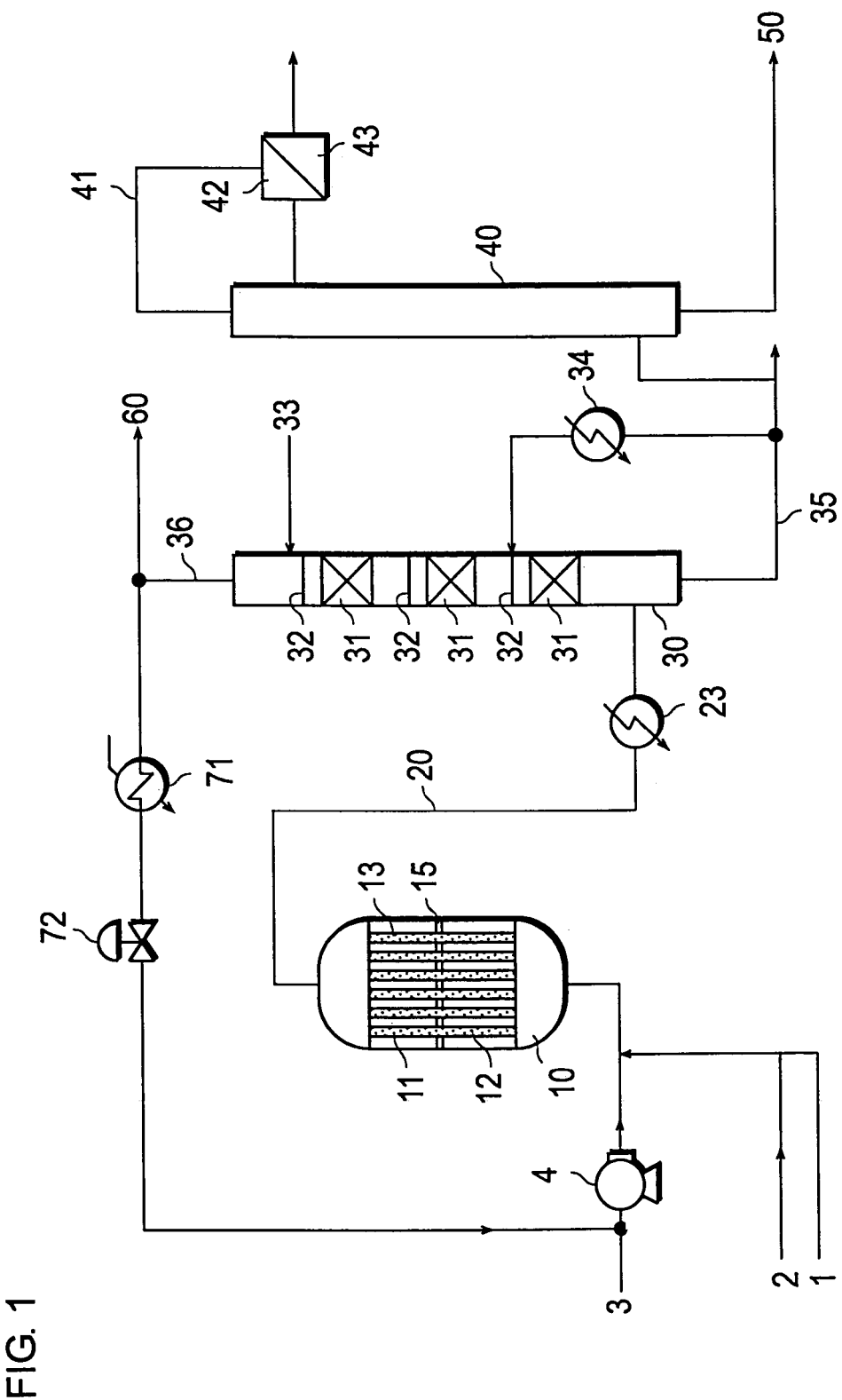
FIG. 1 is a flow sheet illustrating part of a process for producing acrylic acid by the use of a single reactor having a first reaction zone and a second reaction zone thereof formed by dividing reaction tubes with at least one perforated tube plate.

The first aspect of this invention is a method for the production of acrylic acid comprising a step of introducing a mixed gas containing propylene and molecular oxygen into a first reaction zone packed with a complex oxide catalyst having molybdenum and bismuth as essential components and oxidizing propylene and obtaining an acrolein-containing gas, a step of introducing said acrolein-containing gas into a second reaction zone packed with a complex oxide catalyst having molybdenum and vanadium as essential components and obtaining an acrylic acid-containing gas, and a step of introducing said acrylic acid-containing gas into an acrylic acid absorption column and causing it to contact an absorbent thereby obtaining an acrylic acid-containing solution which comprises the steps of (a) said first reaction zone and said second reaction zone being formed by dividing reaction tubes with at least one perforated tube plate, (b) said mixed gas for introduction into said first reaction zone having a propylene concentration in the range of 7–15 vol. % and a water concentration in the range of 0–10 vol. %, and (c) said acrylic acid-containing solution absorbed in said acrylic acid absorption column having a water concentration in the range of 1–45 wt. %.

For the sake of heightening the yield of production, it is effective to increase the concentration of propylene and necessary as well to increase the concentration of oxygen. Since the absorption of the heat of reaction consequently generated is not sufficient and the control of the reaction is difficult, however, there are times when the reaction of catalytic gas phase oxidation will not be accomplished in a stable manner on account of the relation thereof with the explosive range. In this case, the explosive range mentioned above can be avoided by predetermining an explosive range conforming to the conditions of an assumed operation and, when the operation is found to fall in the predetermined explosive range, introducing into the reaction system such a diluting gas as propane which can narrow this range. It has been found that by simultaneously adjusting the water concentration of the acrylic acid-containing solution which has absorbed the produced acrylic acid to a level in the range of 1–45 wt. %, it is made possible to prevent the generation of a polymer in the absorption column and at the subsequent steps and mitigate the operation, of purification at the subsequent steps. The term "purification" as used in this invention embraces distillation, stripping, crystallization, extraction, absorption, dephlegmation, etc. The term "distillation" means a method which consists in heating a solution to the boiling point thereof and separating from the solution a volatile component contained therein, the term "stripping" means a method which consists in supplying a stripping gas into a liquid and effecting transfer of an object substance in the liquid phase into a gas phase, the term "crystallization" means a method which consists in separating an object substance in the form of crystals, the term "extraction" means a method which consists in separating an object substance by dissolving it in a solvent, the term "absorption" means a method which consists in separating an object substance in a gas phase or a liquid phase by causing it to contact a liquid or a solid, and the term "dephlegmation" means a method which consists in separating an object substance by causing part of a gas or vapor to condense. The term "low boiling substance" as used in this invention refers to a substance which has a lower boiling point than acrylic acid in the standard condition and the term "high boiling substance" refers to a substance which has a higher boiling point than acrylic acid in the standard condition. Now, this invention will be described in detail below.

This invention obtains an acrylic acid-containing gas by introducing propylene into a first reaction zone packed with a complex oxide catalyst having molybdenum and bismuth as essential component thereby oxidizing propylene and forming an acrolein-containing gas and introducing the acrolein-containing gas into a second reaction zone packed with a complex oxide catalyst having molybdenum and vanadium as essential components.

The reactor does not need to be particularly restricted but is only required to be capable of performing a reaction of catalytic gas phase oxidation. A shell-and-tube type reactor can be advantageously used because it excels in the efficiency of reaction. The material, size, and quantity of reaction tubes and the distribution of such tubes may be arbitrarily selected. Thus, any of the known test tubes may be used. This invention is characterized by using a reactor which has a first reaction zone and a second reaction zone thereof formed by dividing reaction tubes with at least one perforated tube plate (hereinafter referred to as "single reactor"). The first reaction means a step of oxidizing propylene and converting it mainly into acrolein and the second reaction means a step of oxidizing acrolein into acrylic acid. As for the oxidizing catalyst destined to fill the reaction zone, the first reaction zone is packed with the complex oxide catalyst (i) having molybdenum and bismuth as essential components for obtaining acrolein by oxidizing propylene and the second reaction zone is packed with the complex oxide catalyst (ii) having molybdenum and vanadium as essential components for obtaining acrylic acid by oxidizing acrolein.

One example of the embodiment of this invention using one reactor having the first reaction zone and the second reaction zone thereof partitioned with a perforated tube plate will be explained below with reference to FIG. 1. In FIG. 1, 1 denotes propylene, 2 steam, 3 air, 10 a reactor, 11 a reaction tube, 12 a complex oxide catalyst (i), 13 a complex oxide catalyst (ii), 15 a perforated tube plate, 20 an acrylic acid-containing gas, 23 a heat exchanger, 30 an absorption column, 31 a packed bed, 32 a distributor, 33 an absorbent, 34 a cooler, 35 an acrylic acid-containing solution, 36 exhaust gas, 40 a dehydrating column, 41 a distilled vapor, 42 a solvent phase, 43 a water phase, 50 a subsequent step, 60 waste gas, 71 a heat exchanger, and 72 a flow controller.

First, the propylene 1 as the raw material gas is supplied together with the steam 2 and the air 3 containing molecular oxygen to the reactor 10. In the reactor 10, the reaction tube 11 is packed with the complex oxide catalyst (i) 12 and the complex oxide catalyst (ii) 13 as oxidizing catalysts and the catalyst (i) oxides propylene and obtains acrolein and then the catalyst (ii) oxides acrolein and obtains the acrylic acid-containing gas 20. Subsequently, the acrylic acid-containing gas 20 is introduced into the acrylic acid absorption column 30 and is absorbed by the absorbent 33. The bottom liquid of the column as the acrylic acid-containing solution 35 is partly circulated to the acrylic acid absorption column 30 as kept cooled with the cooler 34, and the rest is introduced into the dehydrating column 40 and subjected therein to a dehydrating treatment. The distilled vapor 41 from the dehydrating column 40 is condensed by the condenser disposed at the top of the dehydrating column 40 and then the resultant condensate is separated into the solvent phase 42 and the water phase 43. The solvent phase 42 is circulated to the dehydrating column 40 and the water phase 43 may be reused as the absorbent 33. The bottom liquid of the dehydrating column 40 is supplied to the subsequent step 50 and further subjected to purification for the separation of the low boiling substance and the high boiling substance. The exhaust gas 36 from the absorption column 30 may be wholly disposed of as the waste gas 60. Alternatively, part of the exhaust gas 36 may be circulated by the blower 4 to the reactor 10 as a recycle gas and only the remainder thereof may be disposed of as the waste gas 60.

In this invention, the complex oxide catalyst (i) which is used in the first reaction zone is only required to contain molybdenum and bismuth. A catalyst which is represented by the general formula, $Mo_a$—$Bi_b$—$Fe_c$—$A_d$—$B_e$—$C_f$—$D_g$—$O_x$ (wherein Mo, Bi, and Fe denote molybdenum, bismuth, and iron respectively, A denotes at least one element selected from the group consisting of nickel and cobalt, B denotes at least one element selected from the group consisting of alkali metals and thallium, C denotes at least one element selected from the group consisting of phosphorus, niobium, manganese, cerium, tellurium, tungsten, antimony and lead, D denotes at least one element selected from the group consisting of silicon, aluminum, zirconium and titanium, O denotes oxygen, and a, b, c, d, e, f, g, and x denote atomic ratios respectively of Mo, Bi, Fe, A, B, C, D, and O such that b=0.1–10, c=0.1–10, d=2–20, e=0.001–5, f=0–5, and g=0–30 are satisfied when a=12 is assumed, and x represents the value which is fixed by the states of oxidation of the relevant elements), may be cited as a preferred example.

Then, the complex oxide catalyst (ii) is only required to contain molybdenum and vanadium. A catalyst which is represented by the general formula, $Mo_a$—$V_b$—$W_c$—$Cu_d$—$A_e$—$B_f$—$C_g$—$O_x$ (wherein Mo denotes molybdenum, V denotes vanadium, W denotes tungsten, Cu denotes copper, A denotes at least one element selected from the group consisting of antimony, bismuth, tin, niobium, cobalt, iron, nickel and chromium, B denotes at least one element selected from the group consisting of alkali metals and alkaline earth metals, C denotes at least one element selected from the group consisting of silicon, aluminum, zirconium and titanium, O denotes oxygen, and a, b, c, d, e, f, g, and x denote the atomic ratios respectively of Mo, V, W, Cu, A, B, C, and O such that b=2–14, c=0–12, d=0.1–5, e=0–5, f=0–5, and g=0–20 when a=12 is assumed, and x represents the value which is fixed by the state of oxidation of the relevant elements), may be cited as a preferred example.

The methods for preparing the catalysts to be used in this invention and the methods for mixing the component materials and molding the resultant mixtures do not need to be particularly restricted. They may be selected from the methods and the raw materials which are in popular use. The shapes of the catalysts contemplated by this invention do not need to be particularly restricted. The catalysts may be formed as spheres, circular columns, and cylinders, for example. The methods of molding may be stationary molding, extrusion molding, pellet molding, etc. Further, the catalysts which have catalytic substances deposited on refractory carriers may be used.

In this invention, the propylene concentration in the mixed gas which is introduced into the first reaction zone is preferably in the range of 7–15 vol. %, more preferably in the range of 8–12 vol. %, and particularly preferably in the range of 8–10 vol. %. If the propylene concentration falls short of 7 vol., the shortage will possibly result in depressing the efficiency of production and lowering the absorbed acrylic acid concentration. Conversely, if the propylene concentration exceeds 15 vol. %, the excess will possibly result in causing the reactor to enter the explosive range and aggravating the hazardousness of the operation.

The water concentration in the mixed gas to be supplied to the first reaction zone is preferably in the range of 0–10 vol. %, more preferably in the range of 0–7 vol. %, and particularly preferably in the range of 0–6 vol. %. The water to be used is wholly transferred to the absorption column. If the water concentration of the mixed gas exceeds 10 vol. %, therefore, the excess will be at a disadvantage in increasing the water concentration of the bottom liquid of the absorption column. It has been elucidated that an attempt to keep the water concentration of the bottom liquid of the absorption column low results in depressing the efficiency of absorption in the absorption column and heightening the polymerizability of the liquid in the absorption column and the piping of the absorption column. The term "efficiency of absorption (%)" as used herein refers to the magnitude represented as 100×{(AAin-AAout)/AAin}, wherein AAin denotes the amount of acrylic acid introduced into the absorption column and AAout denotes the amount of acrylic acid discharged from the top of the absorption column. According to this invention, the efficiency of absorption of acrylic acid in the absorption column can be made to exceed 95%, preferably 96%, by adjusting the water concentration to a level of not more than 10 vol. %.

The mixed gas mentioned above is required to include therein molecular oxygen. The volume ratio of propylene:molecular oxygen is set in the range of 1:1.0–2.0. Though air is used advantageously as the feed source for molecular oxygen, oxygen-enriched air or pure oxygen may be used as occasion demands.

The other components of the mixed gas are nitrogen, carbon dioxide, and other inert gas. The exhaust gas discharged from the absorption column 30 may be recycled for use in the mixed gas. In this case, the amount of steam, the amount of molecular oxygen, and the amount of other inert gas which are necessary for the composition of the mixed gas may be adjusted by the amount of the recycled gas.

In the first reaction zone, the mixed gas of the composition mentioned above is supplied at a space velocity in the range of 500–3,000 $h^{-1}$ (STP) per 1 $m^3$ of the catalyst (i) under a reaction pressure in the range of normal pressure to 0.5 MPa (gauge pressure). The reaction temperature is controlled at a level in the range of 250–450° C., preferably in the range of 300–380° C.

The acrolein-containing gas which is discharged from the first reaction zone is introduced in its unmodified form into the second reaction zone. The acrolein-containing gas is supplied to the second reaction zone at a space velocity in the range of 300–5,000 $hr^{-1}$ (STP) per 1 $m^3$ of the catalyst (ii) under a reaction pressure in the range of normal pressure to 0.5 MPa (gauge pressure). The reaction temperature is controlled at a level in the range of 200–400° C., preferably in the range of 220–380° C. The water concentration in the mixed gas supplied to the first reaction zone can be determined by gas chromatography, by the Carl-Fischer method, or by the use of a hygrometer. The water concentration of the mixed gas may be directly measured. Otherwise, it may be found by measuring the water concentrations of various gases introduced into the first reaction zone and subjecting the results of the measurement to calculation.

The acrylic acid-containing gas 20 which is obtained by the reaction of catalytic gas phase oxidation has a temperature in the range of 200–350° C. Preferably, it is cooled to a temperature in the range of 100–300° C., particularly in the range of 130–270° C. before it is supplied to the absorption column 30. As the heat exchanger 23 to be used for lowering the temperature, any of the known heat exchangers may be used. This cooling must be prevented from lowering the temperature of the mixture of reaction gases below the dew point of the mixture. When the reaction gas has already fallen in a proper range of temperature, the cooling is not necessary as a matter of course.

In this invention, the acrylic acid-containing gas 20 is supplied to the absorption column 30 and subjected therein to the treatment of absorption by the use of the absorbent 33. The acrylic acid-containing gas which is guided to the absorption column 30 generally contains acrylic acid in the range of 10–30 wt. %, acetic acid in the range of 0.2–5 wt. %, and water in the range of 5–15 wt. %. The conditions for the absorption including the composition of component gases for the reaction gas, the composition of the absorbent, and the temperature of absorption may be arbitrarily selected on the condition that they make the water concentration of the acrylic acid-containing solution 35 in the bottom liquid of the acrylic acid absorption column fall in the range of 1–45 wt. %. The water concentration of the bottom liquid of the column is more preferably in the range of 1–25 wt. % and particularly preferably in the range of 1–20 wt. %. The water concentration falling short of 1 wt. % is difficult to obtain and is at a disadvantage in increasing the amount of acrylic acid to be lost. Conversely, if the water concentration exceeds 45 wt. %, the excess will be at a disadvantage in requiring the apparatus used at the subsequent steps such as the distillation column to be enlarged and suffering the amount of the dehydrating liquid and the amount of the waste water to increase as well. Further, the liquid has the highest polymerizability when the mass ratio of acrylic acid to water in the mixture is about 1:1 and the solution tends to generate a polymer in the absorption column and at the subsequent steps. Moreover, when the dehydration is effected by azeotropic distillation as illustrated in the diagram, the increase in the amount of the water partially condensed in the dehydrating column 40 induces polymerization of acrylic acid and tends to give rise to a polymer. Specifically, for the sake of dehydrating the acrylic acid-containing solution 35, the treatment of azeotropic dehydration which is performed in the presence of an azeotropic solvent is generally resorted to. If the water concentration exceeds 45 wt. %, the excess will induce conspicuous oil-water phase separation between the hydrophobic azeotropic dehydrating solvent and water, render the dispersion of a polymerization inhibitor uneven, and dispose the acrylic acid to polymerize.

As the acrylic acid absorption column 30, any of the known columns such as plate column, packed column, spray column, etc. may be used. The plate column or the packed column proves preferable where the acrylic acid concentration in the acrylic acid-containing gas to be treated is high and the polymerization in the column needs to be prevented effectively.

In the case of the packed column, for example, it is preferable to place a packing material having a relatively high efficiency of absorption of acrylic acid on the upstream side of the flow of the absorbent within the column and a packing material having a relatively low ability of forming the polymer of acrylic acid and/or plates on the downstream side. The expression "relatively high(low)" means that when a plurality of packing materials are used, a given packing material has a higher (lower) performance than the other packing materials. The statement "a packing material having a relatively low ability of forming a polymer" means that when a plurality of packing materials are used each in packing the acrylic acid absorption column, a given packing material has a lower ability to form a polymer than the other packing materials. Generally, since the absorbent and the acrylic acid-containing gas are advanced into counter-current contact, the upper part of the acrylic acid absorption column constitutes the upstream side and the bottom side of the acrylic acid absorption column constitutes the downstream side. In the various packing materials and plates which are available for packing acrylic acid absorption columns, the gauze type regular packing material ranks at the top and the sheet type regular packing material, the irregular packing material, the grid type regular packing material, and the plates follow it in the descending order in terms of the efficiency of absorption in any ordinary column. The plates which are endowed with high performance equal the sheet type regular packing material and the irregular packing material. In terms of the ease with which acrylic acid polymerizes, the gauze type regular packing material ranks at the top and the sheet type regular packing material, the irregular packing material, the grid type regular packing material, and the plates follow it in the descending order. When the gauze type regular packing material is used with a view to heightening the efficiency of absorption, for example, since the gauze type regular packing material is liable to dispose a substance under treatment to polymerize, it poses the problem of polymerization and renders an extended operation impossible. Conversely, when the grid type regular packing material is used, for example, with a view to preventing the polymerization, since this packing material is deficient in the efficiency of absorption, it requires the column to have an unduly large height for the purpose of obtaining an expected efficiency. Thus, by using the gauze type regular packing material on the upstream side of the flow of the liquid containing the solvent in the column and at least one material selected from the group consisting of the sheet type regular packing material, the irregular packing material, the grid type regular packing material, and the plates, particularly preferably the sheet type regular packing material and/or the irregular packing material, on the downstream side, both the ability to prevent polymerization and the efficiency of absorption are satisfied and the extended stable operation is realized. The gauze type regular packings include Sulzer Packing (made by Sumitomo Heavy Industries Co., Ltd.), Technopack (made by Mitsui & Co., Ltd.), and M. C. Pack (made by Mitsubishi Chemical Engineering Co., Ltd.), the sheet type regular packing materials include MELLAPAK (made by Sumitomo Heavy Industries Co., Ltd.), Technopack (made by Mitsui & Co., Ltd.), and M. C. Pack (made by Mitsubishi Chemical Engineering Co., Ltd.), the grid type regular packing materials include Flexigrid (made by KOCH Engineering Co., Inc.), the irregular packing materials include Raschig Rings, Pall Rings, Cascade Mini Rings (made by Dodwell Corp.), and IMTP (made by Norton Corp.), and the plates include sieve tray, valve tray, bubble cap tray, buffle tray, dual flow tray, super flack tray, ripple tray and jet tray. Among other irregular packing materials, Cascade Mini Rings and IMTP which permit nearly regular packing prove particularly favorable because they excel in the ability to prevent polymerization and exhibit a high efficiency of absorption.

The top of the acrylic acid absorption column is generally operated under a pressure exceeding the normal pressure. The pressure in the top of the column (gauge pressure) is properly in the range of 0–0.4 MPa, preferably in the range of 0–0.1 MPa, and particularly in the range of 0–0.03 MPa. If this pressure is lower than 0 MPa (gauge pressure), the shortage will be at a disadvantage in necessitating a vacuum device and entailing a plant cost and a utility cost. Conversely, if the pressure exceeds 0.4 MPa (gauge pressure), the excess will be at a disadvantage in requiring the temperature of the absorption column to be increased considerably with a view to expelling the low boiling substance from the top of the column and exalting the polymerizability of acrylic acid in the absorption column. The temperature of the top of the column is preferred to be generally in the range of 30–80° C. and particularly in the range of 40–70° C.

This invention contemplates adjusting the water concentration of the acrylic acid-containing solution in the range of 1–45 wt. %. Though the method for effecting this adjustment does not need to be particularly restricted, the adjustment can be attained by varying the amount of the absorbent to be introduced. This invention prefers to effect the absorption of acrylic acid by establishing counter-current contact between the acrylic acid containing gas introduced into the absorption column and the absorbent supplied thereto at a mass flow rate of the absorbent properly in the range of 0.1–1.5 times, advantageously in the range of 0.2–1.3 times, and particularly advantageously in the range of 0.3–1.1 times to the mass flow rate of the propylene introduced into the first reaction zone. If the mass flow rate of the absorbent falls short of 0.1 times, the shortage will result in rendering the absorption of acrylic acid difficult, decreasing the quantity of the wetting liquid in the absorption column, and inducing an extreme decline in the efficiency of the operation of the absorption column. The quantity of the wetting liquid of the absorption column is defined by the following formula.

Quantity of wetting liquid $[m^3/m^2 \cdot hr]$ = Flow rate of absorbent per unit time $[m^3/hr]$ / Cross-sectional area of absorption column $[m^2]$ The quantity of the wetting liquid is properly not less than 0.2 $m^3/m^2 \cdot hr$, preferably not less than 0.8 $m^3/m^2 \cdot hr$, and particularly preferably not less than 1.0 $m^3/m^2 \cdot hr$. If the mass flow rate exceeds 1.5 times, the excess will results in increasing the water concentration of the acrylic acid-containing solution which is subjected to absorption of acrylic acid. If the temperature of the absorption column is elevated with a view to fixing the water concentration in the acrylic acid-containing solution at a constant level, this elevation will be at a disadvantage in disposing the acrylic acid to polymerization.

As concrete examples of the absorbent to be supplied, such known solvents as water, organic acid-containing waters, and high boiling inert hydrophobic organic liquids may be cited. These absorbents may be used either singly or in the form of a mixture of two or more members. For this invention, the absorbent is preferred to have water as a main component. The absorbent in the acrylic acid absorption column, for example, possibly has a composition of 0–10 wt. % of acrylic acid, 0–20 wt. % of acetic acid, and 70–100 wt. % of water.

Incidentally, this absorbent is preferred for the purpose of preventing such a polymerizing substance as acrylic acid from polymerization to contain one or more compounds selected from the group consisting of N-oxyl compounds, phenol compounds, manganese salts such as manganese acetate, copper dialkyldithiocarbamates such as copper dibutyl-thiocarbamate, nitroso compounds, amine compounds, and phenothiazine.

The N-oxyl compounds do not need to be particularly restricted but may be selected from such N-oxy compounds which are generally known as polymerization inhibitors for vinyl compounds. Among other N-oxyl compounds, 2,2,6,6-tetramethyl piperidinoxyls represented by the following formula (1):

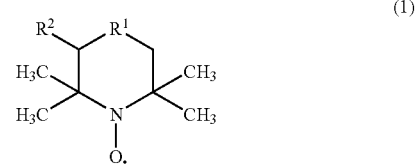

(1)

(wherein $R^1$ denotes $CH_2$, CHOH, $CHCH_2OH$, $CHCH_2CH_2OH$, $CHOCH_2OH$, $CHOCH_2CH_2OH$, CHCOOH, or C=O and $R^2$ denotes a hydrogen atom or $CH_2OH$) are favorably used. Though N-oxyl compounds are usable without being particularly restricted, it is proper to use one or more members selected from among 2,2,6,6-tetramethyl piperidinoxyl, 4-hydroxy-2,2,6,6-tetramethyl piperidinoxyl, and 4,4',4''-tris-(2,2,6,6-tetramethyl piperidinoxyl)phosphite which afford a proper effect of preventing polymerization. Particularly when 2,26,6-tetramethyl piperidinoxyl or 4-hydroxy-2,2,6,6-tetramethyl piperidinoxyl is used as an N-oxyl compound, since it constitutes a stabilizer system without requiring inclusion of a metal in the relevant component, it dismisses the possibility of the metallic parts of the equipment being corroded by the stabilizer and facilitates the disposal of waste liquid as well.

As typical examples of the N-hydorxy-2,2,6,6-tetramethyl piperidine compound, 1,4-dihydroxy-2,2,6,6-tetramethyl piperidine and 1-hydroxy-2,2,6,6-tetramethyl piperidine may be cited. These N-hydroxy-2,2,6,6-tetramethyl piperidine compounds may be used either singly or in the form of a mixture of two or more members.

As concrete examples of the 2,2,6,6-tetramethyl piperidine compound, 2,2,6,6-tetramethyl piperidine and 4-hydroxy-2,2,6,6-tetramethyl piperizine may be cited. These compounds may be used either singly or in the form of a mixture of two or more members. Incidentally, N-hydroxy-2,2,6,6-tetramethyl piperidine compounds and 2,2,6,6-tetramethyl piperidine compounds are possibly contained as impurities in commercial products of N-oxyl compounds. The use of such a commercially available N-oxyl compound results in additional use of an N-hydroy-2,2,6,6-tetramethyl piperidine compound and a 2,2,6,6-tetramethyl piperidine compound.

As concrete examples of the phenol compound, hydroquinone, methoquinone, and (p-methoxyphenol) may be cited. Methoquinone proves advantageous because it excels hydroquinone in the effect of preventing polymerization particularly when it is used in combination with an N-oxyyl compound or a phenothiazine compound.

As concrete examples of the phenothiazine compound, phenothiazine, bis-(α-methylbenzyl)-phenothiazine, 3,7-dioctylphenothiazine, and bis-(α-dimethylbenzyl)phenothiazine may be cited.

The copper salt compound does not need to be particularly restricted but may be selected from various inorganic and organic copper salts. As concrete examples of the copper salt compound, copper dialkyldithiocarbamates, copper acetate, copper naphthenate, copper acrylate, copper sulfate, copper nitrate, and copper chloride may be cited. The copper salt compounds of both univalent and divalent forms are usable. Among other copper salt compounds mentioned above, copper dialkyldithiocarbamates prove particularly favorable from the viewpoint of effect, for example.

As concrete examples of the copper dialkyldithiocarbamate, copper dimethyldithiocarbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyydithiocarbamate, copper methylpentyldithiocarbamate, copper methylhexyldithiocarbamate, copper methylphenyldithiocarbamate, copper ethylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithiocarbamate, copper butylpentyldithiocarbamate, copper butylhexyldithiocarbamate, copper butylphenyldithiocarbamate, copper pentylhexyldithiocarbamate, copper pentylphenyldithiocarbamate, and copper hexylphenyldithiocarbamate may be cited. These copper dialkyldithiocarbamates may be both univalent and divalent copper salts. Among other copper dialkyldithiocarbamates mentioned above, copper dimethyldithiocarabamate, copper diethyldithiocarbamate, and copper dibutyldithiocarbamate prove favorable and copper dibutyldithiocarbamate proves particularly favorable from the viewpoint of effect and ease of procurement.

As concrete examples of the manganese salt compound, manganese dialkyldithiocarbamates (the alkyl group may be any of methyl, ethyl, propy and butyl, and the two alkyl groups may be identical or otherwise), manganese diphenyldithiocarbamate, manganese formate, manganese acetate, manganese octanoate, manganese napthenate, manganese permanganate, and manganese salt compounds of ethylenediamine tetraacetic acid may be cited. These manganese salt compounds may be used either singly or in the form of a mixture of two or more members.

This invention prefers the absorbent to include one or more compounds selected from among N-oxyl compounds, phenol compounds, manganese salts, copper dialkyldithiocarbamates, nitroso compounds, amine compounds, and phenothiazines. The combined use of two or more of these seven kinds of compounds brings about an equal or greater effect of preventing polymerization.

The amount of the polymerization inhibitor to be used does not need to be particularly restricted but may be properly adjusted to suit the conditions of the relevant operation. It is, however, proper to limit the total amount of the polymerization inhibitor to be used in the range of 3–3,500 ppm (by mass) based on the mass of the acrylic acid in the reaction gas to be absorbed. As regards the preferred amounts of the individual polymerization inhibitors to be used, the amount of N-oxyl compound is in the range of 1–500 ppm, the amount of manganese salt compound or copper salt compound is in the range of 1–200 ppm, the amount of nitroso compound is in the range of 1–500 ppm, the amount of phenol compound is in the range of 1–500 ppm, and the amount of phenothiazine compound is in the range of 1–500 ppm respectively based on the mass of acrylic acid in the reaction gas.

Further, the site for the supply of the polymerization inhibitor and the method for the incorporation thereof into the system do not need to be particularly restricted. It is nevertheless proper to supply the polymerization inhibitor through the top of the acrylic acid absorption column. When the polymerization inhibitor is mixed with the absorbent in advance of the supply thereof to the system, it is utilized effectively because it is enabled to be distributed uniformly in the acrylic acid absorption column. It is economical to reuse the absorbent which has been separated in the purifying column.

This invention does not contemplate imposing any restriction on the method for purification subsequent to the step for the absorption of acrylic acid, because it directs adjusting the water concentration of the bottom liquid of the acrylic acid absorption column in a specific range thereby improving the efficiency of absorption and stabilizing the various subsequent steps, and not toward restricting the purification to any specific method.

Generally, the treatment for dehydration is followed by the step for separating a low boiling substance, the step for separating a high boiling substance, and the other steps for purification. This invention permits combination of any of the methods of purification heretofore known to the art. The purification of acrylic acid may be effected not merely by the method of distillation but also by proper combination of stripping, crystallization, extraction, absorption, and partial condensation.

The second aspect of this invention is a method for the production of acrylic acid comprising a step of introducing a mixed gas containing propylene and molecular oxygen into a first reaction zone packed with a complex oxide catalyst having molybdenum and bismuth as essential components and oxidizing propylene and obtaining an acrolein-containing gas, a step of introducing said acrolein-containing gas into a second reaction zone packed with a complex oxide catalyst having molybdenum and vanadium as essential components and obtaining an acrylic acid-containing gas, and a step of introducing said acrylic acid-containing gas into an acrylic acid absorption column and causing it to contact an absorbent thereby obtaining an acrylic acid-containing solution which comprises the steps of (a) said first reaction zone and said second reaction zone being formed by dividing reaction tubes with at least one perforated tube plate, (b) said propylene concentration of said mixed gas introduced into said first reaction zone being in the range of 7–15 vol. % and the water concentration in said mixed gas being in the range of 0–10 vol. %, and (c) said water concentration of said acrylic acid-containing solution obtained in the acrylic acid absorption column being adjusted to a level in the range of 1–45 wt. % by adjusting the amount of an absorbent to be introduced.

This second invention is different from the first invention in respect of the necessary condition of the item (c) mentioned above, namely the point that the adjustment of the water concentration of the acrylic acid-containing solution to a level in the range of 1–45 wt. % is attained by the regulation of the amount of the absorbent to be introduced. The other necessary conditions for the second invention are the same as those of the first invention mentioned above.

The exhaust gas 36 discharged from the top of absorption column 30 contains heat, steam, unreacted propylene, acrolein, and inert gas which are generated by the reaction of catalytic gas phase oxidation. It, therefore, can be recycled as illustrated in FIG. 1 by being heated with the heat exchanger 71, then treated with the flow controller 72 to have the flow rate thereof adjusted in the optimum range, and mixed with the air 3 in advance of the supply thereof to the reactor 10. The composition of the exhaust gas, particularly the water content thereof, however, is readily varied by the temperature of the top of the absorption column. This invention, therefore, requires the amount of the steam contained in the mixed gas to be limited in the range of 0–10 vol. %. The act of changing the amount of the water contained in the discharged gas from the top of the column by varying the temperature of the top of the column is not only unfavorable for the sake of limiting the amount of the steam contained in the mixed gas but also liable, when the temperature of the top of the column is heightened, to give rise to an acrylic acid polymer within the absorption column. In contrast, when the amount of the absorbent is varied, the change of the water content of the acrylic acid-containing solution can be adjusted by varying the amount of the absorbent and the variation of the water content of the gas 36 discharged from the top of the column can be controlled. Specifically, the second invention similarly to the first invention is preferred to effect the absorption of acrylic acid by establishing counter-current contact between the acrylic acid including gas introduced into the absorption column and the absorbent supplied thereto at a mass flow rate of the absorbent properly in the range of 0.1–1.5 times, advantageously in the range of 0.2–1.3 times, and particularly advantageously in the range of 0.3–1.1 times to the mass flow rate of the propylene introduced into the first reaction zone.

Incidentally, the expression "by the amount of the absorbent to be introduced" conveys a double meaning, i.e. that the water concentration is controlled in the range of 1–45 wt. % and that, even when the water concentration remains in the range of 1–45 wt. %, the variation thereof is further restrained within a constant range. The significance of the first meaning is as already explained in the first aspect of the invention. In contrast, the significance of the second meaning resides in the fact that the variation in the down stream of the process of production can be efficiently restrained because the variation of the composition of the bottom liquid of the acrylic acid absorption column constituting the upstream of the process is diminished. In the production of acrylic acid, since numerous steps including a step for separation of a low boiling substance, a step for separation of a high boiling substance, and other steps for purification are continuously carried out in addition to the step for absorption of acrylic acid and the step for dehydration mentioned above, a change in the water content of the bottom liquid of the acrylic acid absorption column, for example, results in varying the amount of the dehydrating solvent used in the subsequent step for dehydration, the temperature and the pressure in the interior of the dehydrating column, the amount of the polymerization inhibitor to be used, and the amounts of the solvent phase 42 and water phase 43 to be recovered and recycled from time to time. The change further results in varying the acrylic acid concentration of the bottom liquid of the dehydrating column and the amount of the polymerization inhibitor to be added and varying the conditions of the subsequent separation of the high boiling substance. The variations in these conditions entail the occurrence of acrylic acid polymer at the step of purification and form a cause for degrading the quality of the product. This invention, therefore, has been directed toward producing acrylic acid with high degree of purification by adjusting the water concentration of the acrylic acid-containing solution in a prescribed range in the upstream of the series of steps mentioned above thereby simplifying and conveniencing the treatments at the subsequent downstream series of steps and restraining the variations as well.

The purpose of enabling the water concentration of the acrylic acid-containing solution already falling in the range of 1–45 wt. % to be further controlled in a constant range such as, for example, the range of 20±1 wt. % may be accomplished by measuring the water concentration of the bottom liquid of the absorption column and varying the amount of the absorbent to be incorporated based on the result of the measurement. As the methods for measuring the water concentration of the bottom liquid of the absorption column, a method which finds the water concentration from the change in the electric conductivity of the bottom liquid of the column and a method which finds the water concentration by acidimetry are available in addition to gas chromatography and Carl Fischer process.

The acrylic acid which has been obtained by the first or the second invention may be supplied to a step for the production of polyacrylic acid (salt) to manufacture polyacrylic acid (salt) and the polyacrylic acid thus obtained may be used for further manufacturing a water absorbing resin, for example. The third aspect of this invention, therefore, is a method for the production of polyacrylic acid comprising using the acrylic acid obtained by the method mentioned above.

The process for producing polyacrylic acid (salt) is enabled to produce polyacrylic acid (salt) by introducing the acrylic acid to the step for neutralization, the step for polymerization, the step for drying, and the step for cooling sequentially in the order mentioned and subjecting the acid to the relevant treatments. This process affords polyacrylic acid when it elects to omit the neutralization of acrylic acid. For this process, therefore, the step for neutralization mentioned above constitutes an arbitrary item. The process is allowed to perform a necessary treatment on the flow of the acrylic acid with a view to improving varying solid state properties. It may include a cross-linking step during or after the step for polymerization, for example.

The step for neutralization is an arbitrary additional item for this process. As a concrete example of this step, a method which consists in mixing acrylic acid or a resultant polyacrylic acid (salt) with a prescribed amount of a basic substance in the form of powder or aqueous solution may be cited. The method for this mixture does not need to be particularly restricted but may be selected from among the known methods. Incidentally, the step for neutralization may be carried out prior to polymerization (the neutralization with a monomer), during the course of polymerization, or subsequently to polymerization (the neutralization with a gel). Optionally, it may be carried out both before and after the polymerization. In the illustrated example, the process is depicted as carrying out the step for polymerization subsequently to the step for neutralization. When the step for neutralization is carried out subsequently to the step for polymerization, the construction of the apparatus may be properly modified to suit the flow of the process. The device for polymerization and the device for neutralization may be identical or not identical.

The basic substance to be used for neutralizing may be properly selected from such known basic substances as, for example, carbonates or bicarbonates, hydrides of alkali metals, ammonia, and organic amines. The ratio of neutralization of acrylic acid does not need to be particularly restricted. The neutralization may be adjusted so that the ratio thereof will reach a level in the range of 30–100 mol %, preferably in the range of 50–80 mol %. When the heat of the reaction of neutralization is required to be removed, this removal may be attained by using an arbitrary cooling means, namely by introducing the product of neutralization into such a cooling device as a cooling column, for example. When the liquid thermal medium supplied via the line 4a is adopted as a refrigerant, it has the advantage of lowering the cost of cooling.

The acrylic acid (salt) solution resulting from the neutralization, when necessary, is introduced into the step for polymerization. The method for effecting the polymerization at this step does not need to be particularly restricted. When the polymerization is effected with a radical polymerization initiator, it may resort to any of the known methods of polymerization such as radiation-induced polymerization, electron beam-induced polymerization, and ultraviolet light-induced polymerization using a photosensitizer. At the step for polymerization, the acrylic acid, when necessary, may be polymerized to form an aqueous acrylic acid (salt) solution having an acrylic acid concentration of preferably not less than 10 wt. % and more preferably not less than 20 wt. % and preferably not more than 80 wt. % and more preferably not more than 70 wt. %, prior to the polymerization.

In this invention, various conditions such as the kind of polymerization initiator and the conditions of polymerization may be arbitrarily selected. Such known additives as, for example, the cross-linking agent and other monomers and even the water-soluble chain transfer agent and hydrophilic macromolecular compound may be incorporated, as occasion demands. For the step of polymerization, a reactor or a device which is arbitrarily selected may be used. The polymerization device does not need to be particularly restricted but may be selected properly from among those which are in popular use.

The polyacrylic acid (salt) which results from the polymerization is generally a polymer in the form of a hydrogel. It is subjected further to a step for drying for the purpose of expelling the water contained therein. The method for drying this polymer does not need to be particularly restricted. The polymer may be dried at a properly selected temperature, preferably in the range of 70–230° C. by using any of such known drying devices as the hot air drier, fluidized-bed drier, drum drier, and Nauter type drier. As the thermal medium to be supplied to the step for drying, the steam which is discharged from the step for te production of acrylic acid, particularly the heat of reaction obtained from the device for catalytic gas phase oxidation, may be utilized.

The hydrogel of polyacrylic acid (salt), namely the hydrated polymer, is thermally dried by using any of various drying devices in popular use. The hydrogel may be dried by using such a heat conduction type drier as the drum drier or paddle drier and exposing this hydrogel to the heating surface of the drier which has been dried with steam. For the sake of decreasing the residual monomer and ensuring the efficiency of drying, the hot air conduction drying which is effected by direct exposure of the hydrogen to the steam proves favorable. Specifically, by drying the hydrogel with a hot air, namely a gas containing steam, at a dew-point temperature of not lower than 50° C., preferably not lower than 60° C. and not higher than 90° C., preferably not higher than 80° C. and at a temperature of not lower than 100° C., preferably not lower than 150° C. and not higher than 200° C., preferably not higher than 180° C., it is made possible to decrease the residual monomer and increase a water absorption capacity of the polyacrylic acid (salt). The duration of the drying may be properly selected generally in the range of one minute to three hours, preferably in the range of five minutes to one hour.

The polyacrylic acid (salt) which results from the step for drying still remains at an elevated temperature when it is discharged from the drying column. Properly, it is cooled at the step for cooling to a correct temperature in the range of room temperature–90° C., preferably in the range of 40° C.–80° C. Though the method for cooling the polyacrylic acid (salt) does not need to be particularly restricted, the drying may be attained by blowing cold wind thereon or introducing it into an arbitrary cooling device such as the refrigerator.

The polyacrylic acid (salt) which has been cooled to the expected temperature may be used as it is. It may further undergo granulation or pulverization to an expected shape or further incorporate therein various additives such as reducing agent, spice, and binder so as to suit the purpose for which it is finally used.

For this invention, the polyacrylic acid (salt) which has been dried is preferred to be cooled. When the hydrogel is fragmented to a size in the approximate range of one to several mm and then dried, for example, the polyacrylic acid (salt) arising after drying is in the form of dry particles measuring approximately in the range of one to several mm. Generally, the dry particles occurring after drying are in the form of an aggregate, depending on the kind of method employed for the drying. When the dry polyacrylic acid (salt) is pulverized or further classified, as occasion demands, to form a polyacrylic acid (salt) powder having a weight average particle diameter in the range of 10–1,000 μm, preferably in the range of 100–800 μm and the powder is further made, when necessary, to incorporate therein various modifiers such as, for example, the aqueous solution of a surface cross-linking agent, granulation binder, and deodorant, it is made possible by the application of a cooling step not only to improve the efficiency of pulverization and sharpen the particle size distribution but also to improve the various solid stage properties of a water absorbing resin such as, for example, the water absorption capacity of the polyacrylic acid (salt) under pressure while restraining the dispersion among the individual particles of the powder because the modifiers can be uniformly added to the powder.

Experiments

Now, this invention will be described more specifically below with reference to working examples thereof.

REFERENCE EXAMPLE 1

Preparation of Catalyst

A molybdenum-bismuth type catalyst was prepared as the catalyst for use in the first reaction zone by following the procedure of Example 1 of the official gazette of JP-A-2000-325795. It will be designated as Catalyst (I) herein below. A molybdenum-vanadium type catalyst was prepared as the catalyst for use in the second reaction zone by following the procedure of Example 1 of the official gazette of JP-A-08-206504. It will be designated as Catalyst (II) herein below.

Conversion ratio of propylene (%) =
  100 × [(Number of moles of reacted propylene)/
  (number of moles of supplied propylene)]

Yield of acrolein (%) = 100 × [(Number of moles of formed acrolein)/
  (number of moles of supplied propylene)]

Yield of acrylic acid (%) =
  100 × [(Number of moles of formed acrylic acid)/
  (number of moles of supplied propylene)]

EXAMPLE 1

A reactor which was covered with a jacket for circulation of thermal medium, and provided with reaction tubes measuring 25 mm in inside diameter and 7,000 mm in length therein and inserted a perforated tube plate having a thickness of 75 mm in a position of 3,500 mm from the lower part of the jacket was used. The plate divides the reactor into two vertical parts, an upper one and a lower. The resultant reaction zone (the lower part acts as a first reaction zone and the upper part acts as a second reaction zone) which allowed the temperatures of the thermal media for the upper and the lower parts thereof to be controlled by circulating the thermal media respectively to the upper and the lower parts. It was packed sequentially from the lower part to the upper part of the reaction tube with (1) ceramic balls alone having an average diameter of 5 mm, (2) a mixture formed by mixing the catalyst (I) and ceramic balls of an average diameter of 5 mm at a volume ratio of 70:30, (3) the catalyst (I) alone, (4) Raschig rings made of stainless steel and measuring 5 mm in outside diameter, 4.5 mm in inside diameter, and 6 mm in length, (5) a mixture formed by mixing the catalyst (II) and ceramic balls of an average diameter of 5 mm at a volume ratio of 75:25, and (6) the catalyst (II) alone in the order mentioned to form layers measuring 250 mm, 700 mm, 2,300 mm, 500 mm, 600 mm, and 1,900 mm respectively.

To the first reaction zone, a mixed gas comprising 8.0 vol. % of propylene, 14.4 vol. % of $O_2$, and 5.0 vol. % of $H_2O$ (the balance formed of $N_2$, propane, etc) was supplied at a space velocity of 1,250 $hr^{-1}$ (STP) in the first reaction zone.

At this time, the reaction was continued while the temperatures of the thermal media to the first reaction zone and the second reaction zone were so controlled as to adjust the conversion ratio of propylene in the range of 97±0.5 mol % and the yield of acrolein in the range of 1±0.5 mol % under the second reaction zone outlet pressure of 0.15 MPa (absolute pressure). After the elapse of 100 hours following the start of the reaction, the yield of acrylic acid was 87.0 mol %. The acrylic acid-containing gas obtained at this point was introduced at a temperature of 170° C. into an acrylic acid absorption column having 14 steps as a theoretical number of steps to absorb the acrylic acid therein with an absorbent water containing 1.8 wt. % of acrylic acid, 5.6 wt. % of acetic acid, and such an amount of hydroquinone as equaled 200 wt. ppm based on the amount of the acrylic acid in the acrylic acid-containing gas introduced into the absorption column. When the amount of the absorbent was so adjusted as to fix the water concentration of the bottom liquid of the absorption column at 25 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent/propylene=0.9.

The efficiency of absorption at this time was 98.3%. The absorption column was operated for one week without inducing any rise in the pressure loss in the column and the neighborhood. When the column was then opened and inspected, the inspection did not detect a polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 11.5 hrs. This rise of the viscosity is so related with the length of the time that precedes the start of polymerization. The short time indicates that the solution polymerizes easily and the long time indicates that the solution polymerizes only with difficulty.

EXAMPLE 2

A reaction was performed by following the procedure of Example 1 while changing the composition of the mixed gas supplied to the first reaction zone to 9.0 vol. % of propylene, 16.2 vol. % of $O_2$, and 2.9 vol. % of $H_2O$ (the balance formed of $N_2O$, propane, etc.). After the elapse of 100 hours following the start of the reaction, the yield of acrylic acid was 86.5 mol %. The acrylic acid-containing gas obtained at this point was introduced at a temperature of 168° C. into an acrylic acid absorption column having 14 steps as a theoretical number of steps to absorb the acrylic acid therein with an absorbent water containing 1.8 wt. % of acrylic acid 6.0 wt. % of acetic acid, and such an amount of hydroquinone as equaled 200 wt. ppm based on the amount of the acrylic acid in the acrylic acid-containing gas introduced into the absorption column. When the amount of the absorbent was so adjusted as to fix the water concentration of the bottom liquid of the absorption column at 21 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent/propylene=0.8.

The efficiency of absorption at this time was 98.5%. The absorption column was operated for one week without inducing any rise in the pressure loss in the column and the neighborhood. When the column was then opened and inspected, the inspection did not detect a polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 13.2 hrs.

EXAMPLE 3

The same reactor as used in Example 1 was packed sequentially from the lower part to the upper part of the reaction tube with (1) ceramic balls alone having an average diameter of 5 mm, (2) a mixture formed by mixing the catalyst (I) and ceramic balls having an average diameter of 5 mm at a volume ratio of 55:45, (3) a mixture formed by mixing the catalyst (I) and ceramic balls having an average diameter of 5 mm at a volume ratio of 70:30, (4) the catalyst (I) alone, (5) Raschig rings made of stainless steel and measuring 5 mm in outside diameter, 4.5 mm in inside diameter, and 6 mm in length, (6) a mixture formed by mixing the catalyst (II) and ceramic balls having an average diameter of 5 mm at a volume ratio of 65:35, (7) a mixture formed by mixing the catalyst (II) and racemic balls having an average diameter of 5 mm at a volume ratio of 80:20, and (8) the catalyst (II) alone in the order mentioned to form layers measuring 250 mm, 500 mm, 500 mm, 2,200 mm, 500 mm, 500 mm, 500 mm, and 2,000 mm respectively.

To the first reaction zone, a mixed gas comprising 10.0 vol. % of propylene, 18.0 vol. % of $O_2$, and 0.9 vol. % of $H_2O$ (the balance formed of $N_2$, propane, etc) was supplied at a space velocity of 1,250 $hr^{-1}$ (STP) in the first reaction zone.

At this time, the reaction was continued while the temperatures of the thermal media to the first reaction zone and the second reaction zone were so controlled as to adjust the conversion ratio of propylene in the range of 97±0.5 mol % and the yield of acrolein in the range of 1±0.5 mol % under the second reaction zone outlet pressure of 0.15 MPa (absolute pressure). After the elapse of 100 hours following the start of the reaction, the yield of acrylic acid was 85.6 mol %. The acrylic acid-containing gas obtained at this point was introduced at a temperature of 167° C. into an acrylic acid absorption column having 14 steps as a theoretical number of steps to absorb the acrylic acid therein with an absorbent water containing 1.8 wt. % of acrylic acid, 6.5 wt. % of acetic acid, and such an amount of hydroquinone as equaled 200 wt. ppm based on the amount of the acrylic acid in the acrylic acid-containing gas introduced into the absorption column. When the amount of the absorbent was so adjusted as to fix the water concentration of the bottom liquid of the absorption column at 17 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent/propylene=0.7.

The efficiency of absorption at this time was 98.6%. The absorption column was operated for one week without inducing any rise in the pressure loss in the column and the neighborhood. When the column was then opened and inspected, the inspection did not detect a polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 15.5 hrs.

EXAMPLE 4

The acrylic acid-containing gas obtained in Example 3 was introduced at a temperature of 167° C. into an acrylic acid absorption column having 14 steps as theoretical number of steps to absorb acrylic acid therein with an absorbent water containing 1.8 wt. % of acrylic acid, 7.1 wt. % of acetic acid, and such an amount of hydroquinone as equaled 200 wt. ppm based on the amount of the acrylic acid in the acrylic acid-containing gas introduced into the absorption column. When the amount of the absorbent water was so adjusted as to fix the water concentration of the bottom liquid of the absorption column at 8 wt. % under the conditions of 62.9° C. in temperature of the top of the acrylic acid absorption column and 0.11 MPa (absolute pressure) in the pressure of the top of the column, an acrylic acid containing solution having a target water concentration was obtained at a mass flow ratio of the amount of the absorbent water/propylene=0.5.

The efficiency of absorption at this time was 97.5%. The absorption column was operated for one week without inducing any rise in the pressure loss in the column and the neighborhood. When the column was then opened and inspected, the inspection detected practically no polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 18.8 hrs.

EXAMPLE 5

The same reactor as used in Example 1 was packed sequentially with the same catalysts to form layers measuring 250 mm, 800 mm, 2,200 mm, 500 mm, 700 mm, and 1,800 mm respectively.

To the first reaction zone, a mixed gas comprising 8.0 vol. % of propylene, 14.4 vol. % of $O_2$, and 9.6 vol. % of $H_2O$ (the balance formed of $N_2$, propane, etc) was supplied at a space velocity of 1,500 $hr^{-1}$ (STP) in the first reaction zone.

At this time, the reaction was continued while the temperatures of the thermal media to the first reaction zone and the second reaction zone were so controlled as to adjust the conversion ratio of propylene in the range of 97±0.5 mol % and the yield of acrolein in the range of 1±0.5 mol % under the second reaction zone outlet pressure of 0.15 MPa (absolute pressure). After the elapse of 100 hours following the start of the reaction, the yield of acrylic acid was 86.3 mol %. The acrylic acid-containing gas obtained at this point was introduced at a temperature of 172° C. into an acrylic acid absorption column having 14 steps as a theoretical number of steps to absorb the acrylic acid therein with an absorbent water containing 1.8 wt. % of acrylic acid, 3.8 wt. % of acetic acid, and such an amount of hydroquinone as equaled 200 wt. ppm based on the amount of the acrylic acid in the acrylic acid-containing gas introduced into the absorption column. When the amount of the absorbent water was so adjusted as to fix the water concentration of the bottom liquid of the absorption column at 40 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent water/propylene=1.1.

The efficiency of absorption at this time was 98.9%. The absorption column was operated for one week without inducing any rise in the pressure loss in the column and the neighborhood. When the column was then opened and inspected, the inspection did not detect a polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 8.2 hrs.

EXAMPLE 6

A reaction was carried out by following the procedure of example 4 while changing the $H_2O$ concentration in the mixed gas supplied to the first reaction zone to 7.9 vol. %. After the elapse of 100 hours following the start of the reaction, the yield of acrylic acid was 86.0 mol %. The acrylic acid-containing gas obtained at this point was introduced at a temperature of 171° C. into an acrylic acid absorption column having 14 steps as a theoretical number of steps to absorb the acrylic acid therein with an absorbent water containing 1.3 wt. % of acrylic acid, 4.4 wt. % of acetic acid, and such an amount of hydroquinone as equaled 200 wt. ppm based on the amount of the acrylic acid in the acrylic acid-containing gas introduced into the absorption column, with the mass flow ratio of the amount of the absorbent water/propylene fixed at 1.6. At this time, the temperature of the top of the acrylic acid absorption column was 73.7° C., the pressure of the top of the column was 0.11 MPa (absolute pressure), the water concentration of the bottom liquid of the absorption column was 25 wt. %, and the efficiency of absorption was 97.1%.

The absorption column was operated for one week without inducing any rise in the pressure loss in the column and the neighborhood. When the column was then opened and inspected, the inspection detected a certain amount of polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 11.6 hrs.

COMPARATIVE EXAMPLE 1

A reaction was carried out by following the procedure of Example 1 while chanting the composition of the mixed gas supplied to the first reaction zone to 6.0 vol. % of propylene, 10.8 vol. % of $O_2$, and 9.9 vol. % of $H_2O$ (the balance formed of $N_2$, propane, etc). After the elapse of 100 hours following the start of the reaction, the yield of acrylic acid was 87.8 mol %. The acrylic acid-containing gas obtained at this point was introduced at a temperature of 172° C. into an acrylic acid absorption column having 14 steps as a theoretical number of steps to absorb the acrylic acid therein with an absorbent water containing 1.8 wt. % of acrylic acid, 4.8 wt. % of acetic acid, and such an amount of hydroquinone as equaled 200 wt. ppm based on the amount of the acrylic acid in the acrylic acid-containing gas introduced into the absorption column. When the amount of the absorbent water was so adjusted as to fix the water concentration of the bottom liquid of the absorption column at 25 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent water/propylene=0.8.

The efficiency of absorption at this time was 95.2%. After the operation of the absorption column had been continued for five days, it was discontinued on account of an increase of the pressure loss in the column and the neighborhood. When the column was opened and inspected, the inspection detected a considerable amount of polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 11.8 hrs.

COMPARATIVE EXAMPLE 2

A reaction was carried out by following the procedure of Example 1 while changing the $H_2O$ concentration in the mixed gas supplied to the first reaction zone to 11.6 vol. %. After the elapse of 100 hours following the start of the reaction, the yield of acrylic acid was 87.4 mol %. The acrylic acid-containing gas obtained at this point was introduced at a temperature of 173° C. into an acrylic acid absorption column having 14 steps as a theoretical number of steps to absorb the acrylic acid therein with an absorbent water containing 1.8 wt. % of acrylic acid, 4.1 wt. % of acetic acid, and such an amount of hydroquinone as equaled 200 wt. ppm based on the amount of the acrylic acid in the acrylic acid-containing gas introduced into the absorption column. When the amount of the absorbent water was so adjusted as to fix the water concentration of the bottom liquid of the absorption column at 25 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent water/propylene=0.8.

The efficiency of absorption at this time was 94.9%. After the operation of the absorption column had been continued for four days, it was stopped on account of an increase in the pressure loss in the column and the neighborhood. When the column was then opened and inspected, the inspection detected a considerable amount of polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 11.8 hrs.

COMPARATIVE EXAMPLE 3

A reaction was carried out by following the procedure of Example 1 while changing the H$_2$O concentration in the mixed gas supplied to the first reaction zone to 9.6 vol. %. After the elapse of 100 hours following the start of the reaction, the yield of acrylic acid was 87.1 mol %. The acrylic acid-containing gas obtained at this point was introduced at a temperature of 171° C. into an acrylic acid absorption column having 14 steps as a theoretical number of steps to absorb the acrylic acid therein with an absorbent water containing 1.8 wt. % of acrylic acid, 3.5 wt. % of acetic acid, and such an amount of hydroquinone as equaled 200 wt. ppm based on the amount of the acrylic acid in the acrylic acid-containing gas introduced into the absorption column. When the amount of the absorbent water was so adjusted as to fix the water concentration of the bottom liquid of the absorption column at 47 wt. % under the conditions of 62.9° C. in temperature of the top of the acrylic acid absorption column and 0.11 MPa (absolute pressure) in pressure of the top of the column, an acrylic acid containing solution having a target water concentration was obtained at a mass flow ratio of the amount of the absorbent water/propylene=1.52.

The efficiency of absorption at this time was 99.0%. The absorption column was operated for one week without inducing any rise in the pressure loss in the column and the neighborhood. When the column was then opened and inspected, the inspection did not detect a polymer within the column, the top, and the piping.

A sample, 5 ml in volume, of the acrylic acid containing solution consequently obtained was placed in a test tube. The test tube was immersed in an oil bath kept at 95° C. The time required for the viscosity of the sample to rise was found to be 6.5 hrs.

The invention claimed is:

1. A method for the production of acrylic acid comprising a step of introducing a mixed gas containing propylene and molecular oxygen into a first reaction zone packed with a complex oxide catalyst having molybdenum and bismuth as essential components and oxidizing propylene and obtaining an acrolein-containing gas, a step of introducing said acrolein-containing gas into a second reaction zone packed with a complex oxide catalyst having molybdenum and vanadium as essential components and obtaining an acrylic acid-containing gas, and a step of introducing said acrylic acid-containing gas into an acrylic acid absorption column and causing it to contact an absorbent water thereby obtaining an acrylic acid-containing solution which comprises the steps of
    (a) said first reaction zone and said second reaction zone being formed in a single reactor by dividing reaction tubes with at least one perforated tube plate,
    (b) said mixed gas for introduction into said first reaction zone having a propylene concentration in the range of 7–15 vol. % and a water concentration in the range of 0–10 vol. %,
    (c) said absorbent water is introduced into said acrylic acid absorption column at a mass flow rate in the range of 0.1–1.5 times the mass flow rate of propylene introduced into said first reaction zone, and
    (d) said acrylic acid-containing solution obtained in said acrylic acid absorption column having a water concentration in the range of 1–45 wt. %.

2. A method according to claim 1, wherein a main component of said absorbent water is water.

3. A method for the production of acrylic acid comprising a step of introducing a mixed gas containing propylene and molecular oxygen into a first reaction zone packed with a complex oxide catalyst having molybdenum and bismuth as essential components and oxidizing propylene and obtaining an acrolein-containing gas, a step of introducing said acrolein-containing gas into a second reaction zone packed with a complex oxide catalyst having molybdenum and vanadium as essential components and obtaining an acrylic acid-containing gas, and a step of introducing said acrylic acid-containing gas into an acrylic acid absorption column and causing it to contact an absorbent water thereby obtaining an acrylic acid-containing solution which comprises the steps of
    (a) said first reaction zone and said second reaction zone being formed in a single reactor by dividing reaction tubes with at least one perforated tube plate,
    (b) said propylene concentration of said mixed gas introduced into said first reaction zone being in the range of 7–15 vol. % and the water concentration in said mixed gas being in the range of 0–10 vol. %,
    (c) said absorbent water to be introduced is 0.1–1.5 times the mass flow amount of propylene introduced into said first reaction zone, and
    (d) said water concentration of said acrylic acid-containing solution obtained in the acrylic acid absorption column being adjusted to a level in the range of 1–45 wt. % by adjusting the amount of an absorbent water to be introduced.

4. A method for the production of polyacrylic acid comprising the step of polymerizing the acrylic acid obtained by the method set forth in claim 1.

5. A method for the production of polyacrylic acid comprising polymarizing the acrylic acid obtained by the method set forth in claim 2.

* * * * *